United States Patent [19]

Flatt et al.

[11] Patent Number: 5,425,780

[45] Date of Patent: Jun. 20, 1995

[54] ANKLE, FOOT, AND LOWER LEG PROSTHETIC DEVICE

[76] Inventors: Wayne P. Flatt, 515 N. Elm St.; Walter J. Lorence, 190 Oak Hills Heights, both of Butler, Pa. 16001

[21] Appl. No.: 66,421

[22] Filed: May 25, 1993

[51] Int. Cl.6 .......................... A61F 2/62; A61F 2/66
[52] U.S. Cl. ........................................ 623/38; 623/49; 623/53; 623/27; 623/54; 403/84
[58] Field of Search ...................... 623/38, 48, 49, 53, 623/35, 38, 27, 54; 403/84, 118

[56] References Cited

U.S. PATENT DOCUMENTS

| | | | |
|---|---|---|---|
| 1,063,175 | 5/1913 | Anderson | 623/48 X |
| 1,285,871 | 11/1918 | Winn | 623/49 |
| 1,316,347 | 9/1919 | Bidou | 623/49 |
| 1,552,569 | 9/1925 | Schurman | 403/84 X |
| 2,699,554 | 1/1955 | Comelli | 623/49 |
| 3,196,463 | 7/1965 | Farneth | 623/49 |
| 3,649,968 | 3/1972 | Prahl | 623/38 |
| 3,790,965 | 2/1974 | Gelbenegger | 623/38 |
| 5,226,918 | 7/1993 | Silagy et al. | 623/32 |
| 5,326,352 | 7/1994 | Ferrier | 623/38 |

FOREIGN PATENT DOCUMENTS

| | | | |
|---|---|---|---|
| 0123374 | 2/1947 | Australia | 623/53 |
| 0497206 | 11/1919 | France | 623/53 |
| 1502061 | 11/1967 | France | 623/38 |
| 2501999 | 9/1982 | France | 623/38 |
| 0682099 | 7/1993 | Switzerland | 403/118 |
| 2069847 | 9/1981 | United Kingdom | 623/35 |
| 2114447 | 8/1983 | United Kingdom | 623/38 |

Primary Examiner—David H. Willse
Attorney, Agent, or Firm—George C. Atwell

[57] ABSTRACT

A prosthetic device for simulating the movements of a natural human ankle and foot throughout all the phases of the gait cycle and which is adapted for the removable attachment to the stump of a lower extremity amputee includes an ankle block member having an aperture in which a universal joint is disposed for allowing the ankle block member to simulate the movements to the anatomical limits of the natural human ankle. Attached to the universal joint and extending upwardly therefrom is an elongated tibial component having an upper tibial end to which is attached a tibial shock member for shock absorption of the prosthetic device during phases of the gait cycle when the prosthetic device strikes any walking surface. The prosthetic device further includes a lower and an upper mounting block which are both attached to a receiver mounted to the flat undersurface of the stump, adjustment of the lower mounting block permitting the pitch of the prosthetic device to match the pitch of the amputee's natural leg so that the prosthetic device can be aligned in gait with the amputee's natural leg for normal walking upon any terrain or surface.

29 Claims, 5 Drawing Sheets

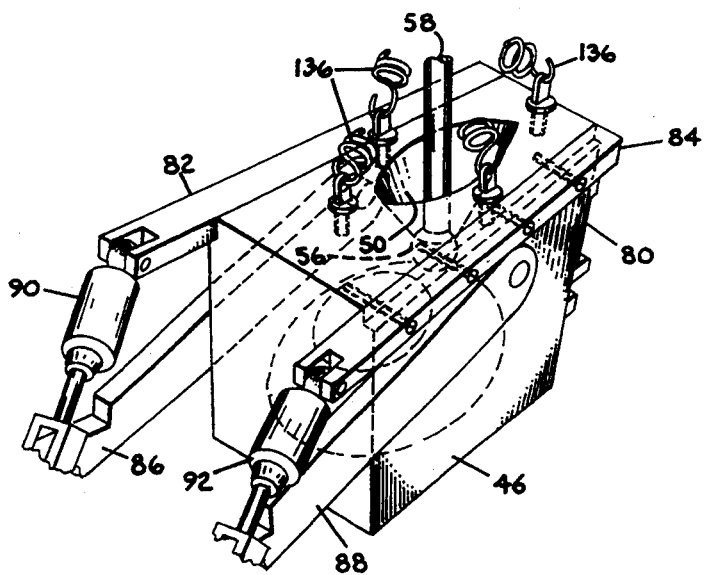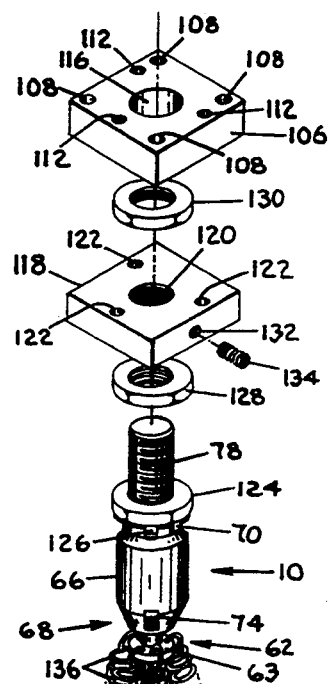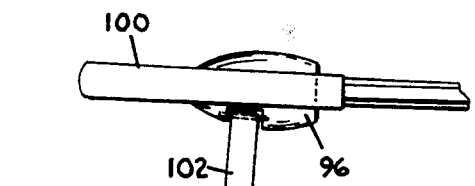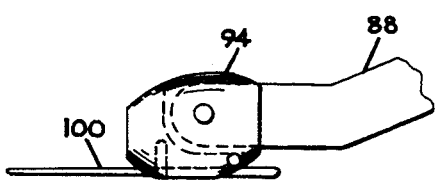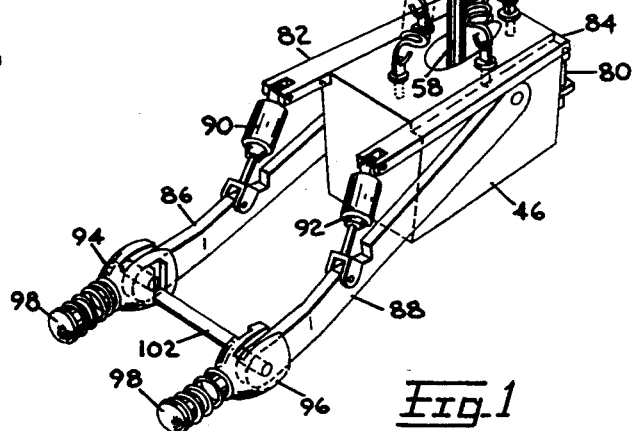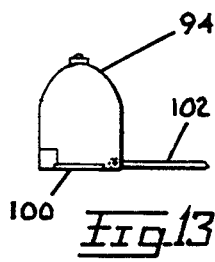

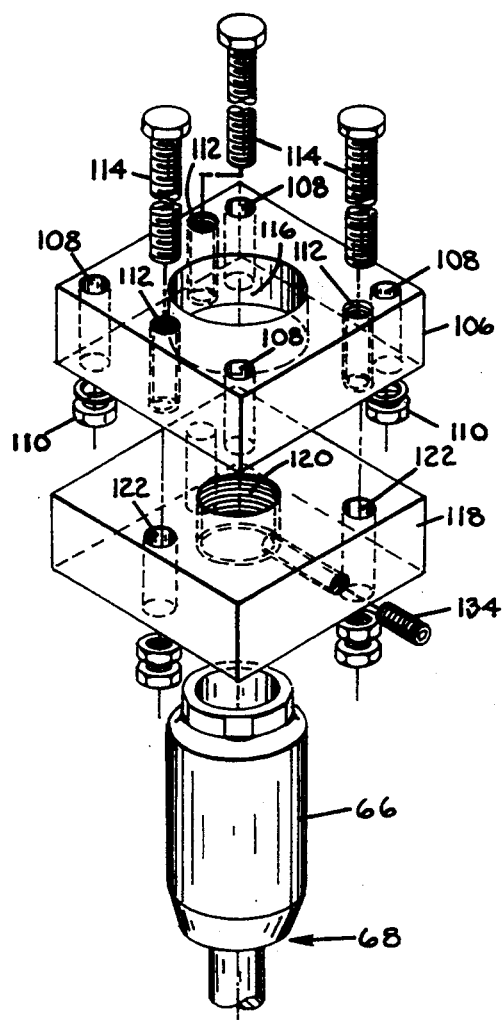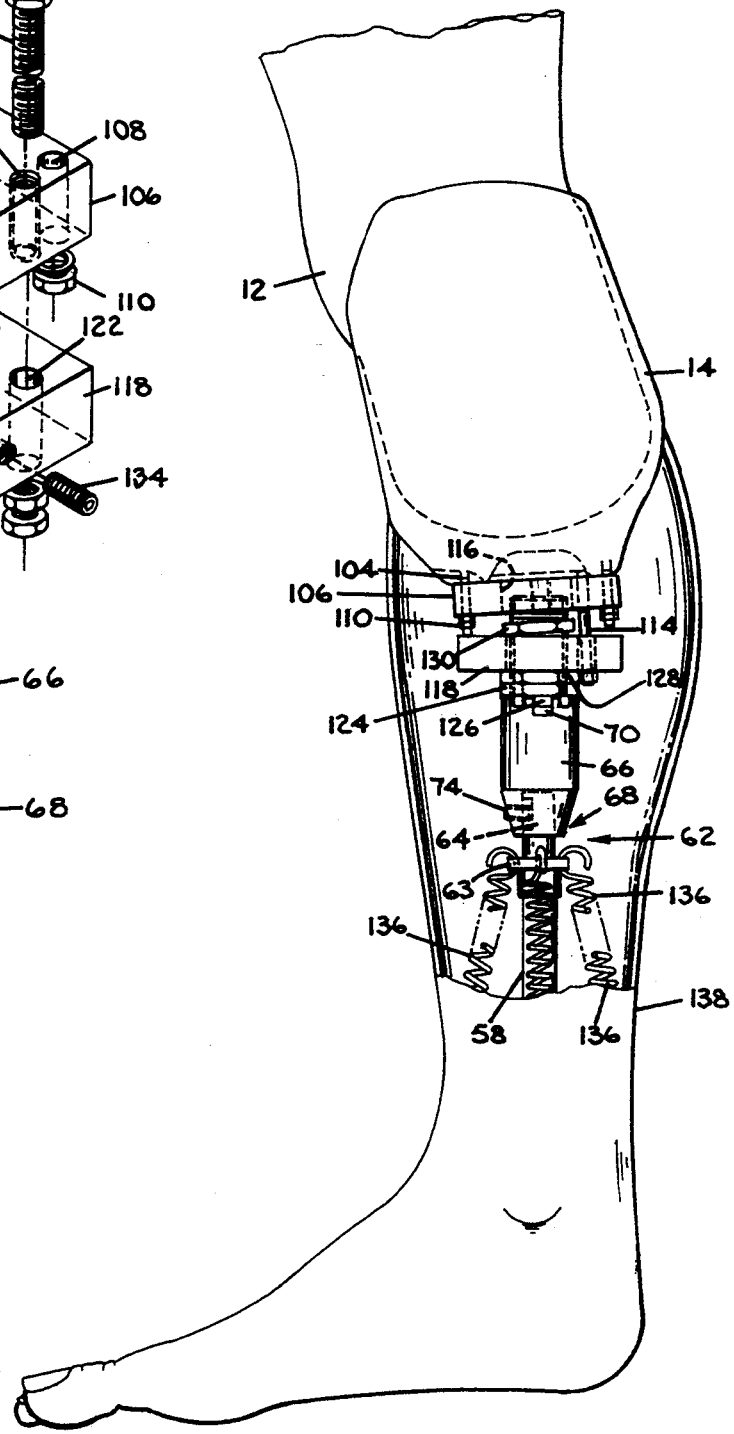

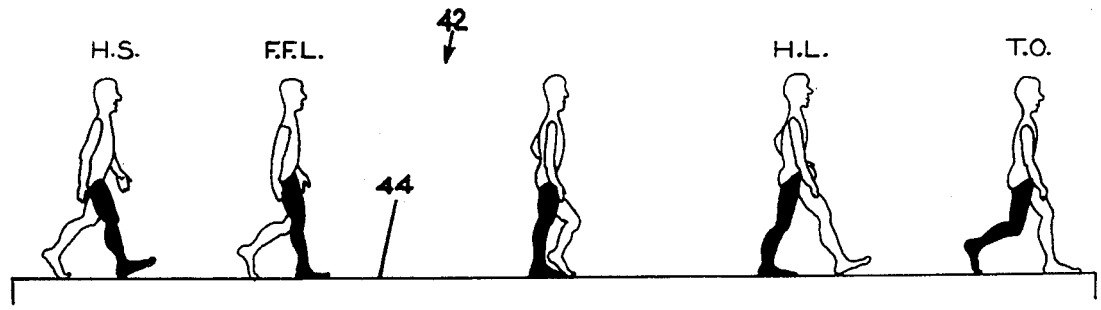
Fig.6
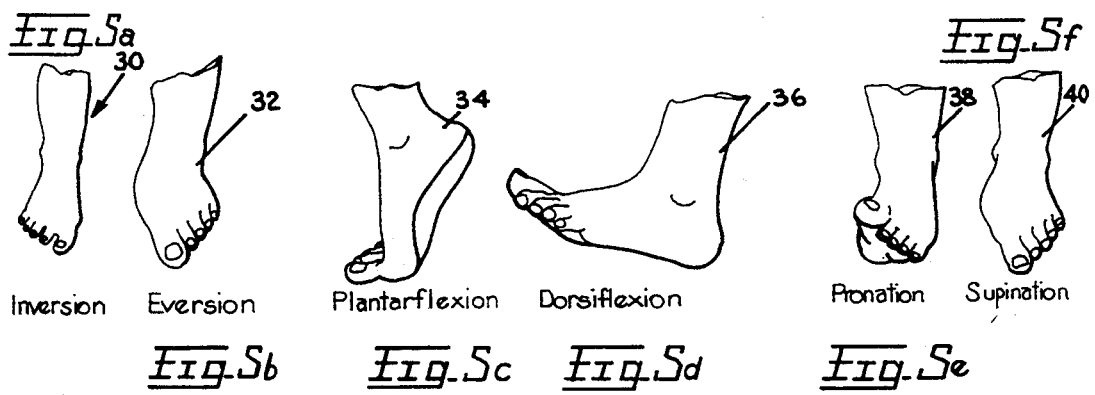
Fig.5a Fig.5f
Inversion  Eversion  Plantarflexion  Dorsiflexion  Pronation  Supination
Fig.5b  Fig.5c  Fig.5d  Fig.5e
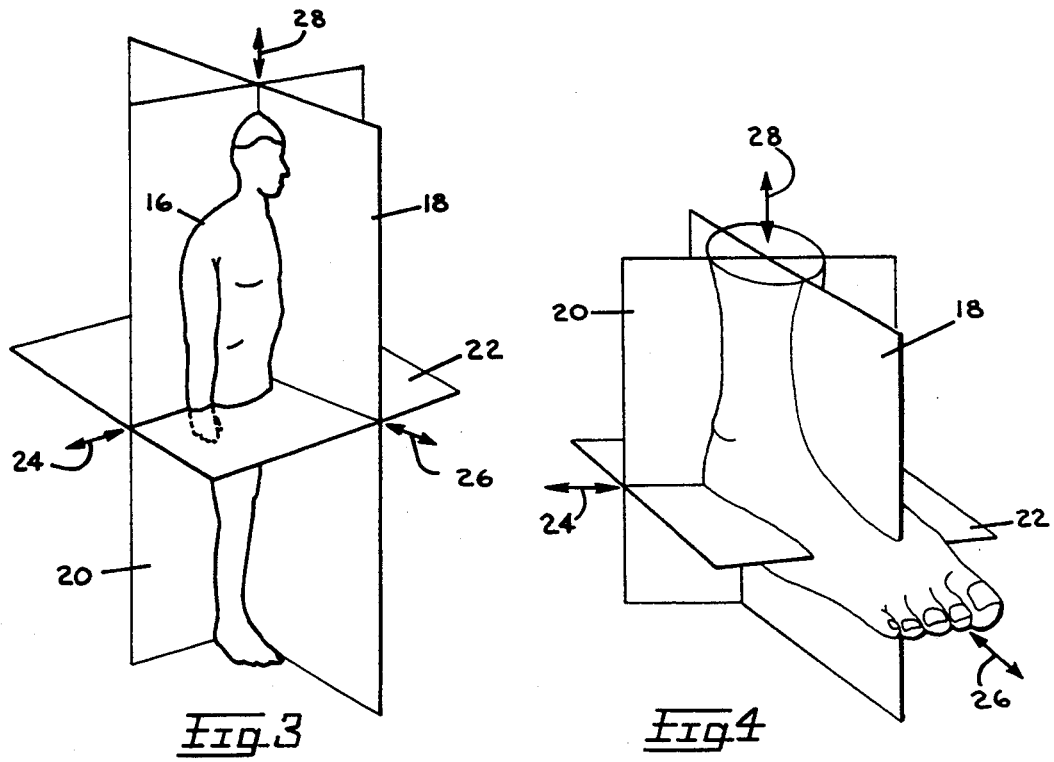
Fig.3  Fig.4

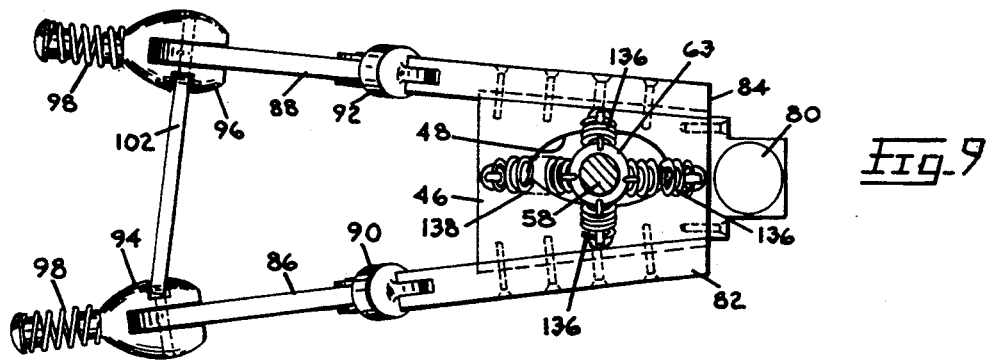
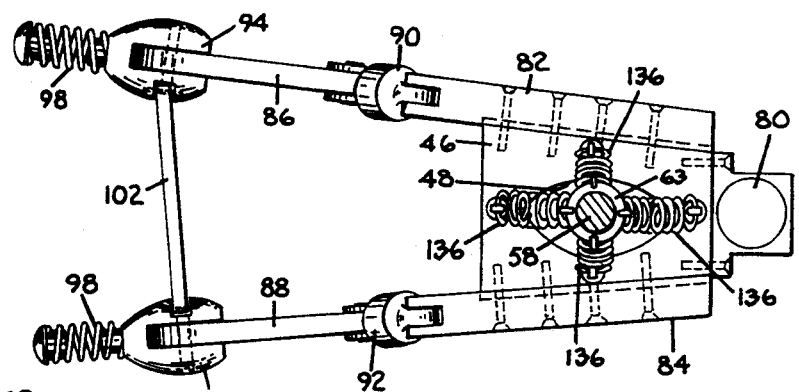
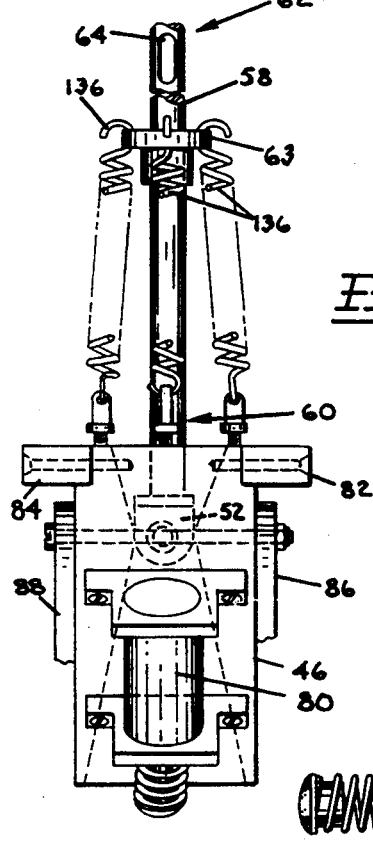
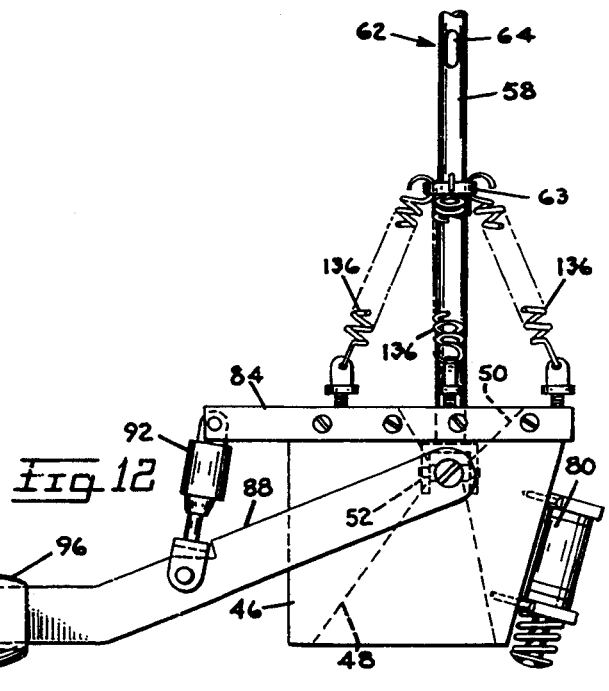

ANKLE, FOOT, AND LOWER LEG PROSTHETIC DEVICE

BACKGROUND OF THE INVENTION

The present invention relates to prosthetic devices, and more particularly pertains to a prosthetic device for a lower extremity amputee which simulates the movements of the amputee's natural foot and ankle.

Prosthetic devices date from antiquity, and the splinting of limbs has been found in mummies from ancient Egypt. Contemporary medical science has made astounding advances since the days of using a stick having a slab of wood tied to its lower end for serving as a splint.

Modern medical science has designed numerous types of prosthetic devices for below-the-knee amputations. Orthotics is the field of medical science which is specifically related to the fabrication and application of prosthetic devices and combines the fields of biomechanics and physiology in designing such prosthetic devices. "Orthoses" is the term which denotes orthopedic appliances used to correct, support, align, prevent, or improve the function of movable body parts. Orthoses are used for individuals having lower extremity bracing problems; prosthetic devices are used for amputees. One of the most common types of amputation is the Syme amputation which results in the removal of the entire foot. As a consequence of the Syme amputation, the prosthesis must incorporate an artificial foot.

The prior art reveals a number of prosthetic devices for a total foot amputee. U.S. Pat. Nos. 41,033 (Vaughan), 264,812 (Wolf), 961,582 (Bradley et al.), 1,174,127 (Davis et al.), 2,529,968 (Sartin), and 2,570,581 (McIntyre) all disclose artificial legs. However, the severe limitations of the aforementioned prior art are readily apparent upon close reading of the patents. None of the devices are easily adjustable for matching the pitch and angle of the artificial leg with the amputee's natural leg. In addition, none of the above devices has the ability to absorb shock occurring during the various phases of the gait cycle.

Moreover, the above-cited devices do not avoid the phenomenon known as Trendelenburg gait (a method of walking with an artificial leg that necessitates swinging the prosthesis laterally and forward in gait). Also, the above-cited devices do not disclose structural elements or means which would permit the amputee to smoothly and without difficulty stand or walk on an uneven surface or terrain.

Therefore, there is a need for a prosthetic device which accomplishes all of the above-described purposes, and is also lightweight, extremely durable, and, since the distance from the ground surface to the stump varies for each respective amputee, adaptable for each respective amputee who will wear the prosthetic device. In addition, there is a need for a prosthetic device which is adjustable for accommodating the natural growth of that portion of the individual's leg remaining after the amputation.

SUMMARY OF THE INVENTION

The present invention comprehends an ankle, foot, and lower leg prosthetic device for lower leg amputees which simulates the biomechanical movements of a natural human foot and ankle to the anatomical limits thereof during the various phases of the gait cycle.

The prosthetic device of the present invention includes a number of structural components which function in concert with each other, the paramount structure being the ankle block member. The ankle block member simulates the movements of a natural human ankle, and has a front side, a rear side, a lateral side, a medial side, and an upper surface. The ankle block member further includes a chamber configured like an hourglass-like aperture extending therethrough and registering with the upper surface. Acting in conjunction with other structural elements which will be hereinafter described, the ankle block member is adapted to act in the three reference planes of the human body (the sagittal plane, the transverse plane, and the frontal plane), and functions to match the anatomical limits of movement of the natural human ankle.

Disposed within the narrowest point of the hourglass-like aperture is a universal joint. An anchoring pin or connecting rod extends medially-to-laterally through this portion of the hourglass-like aperture and mounts the universal joint to the ankle block member. The universal joint allows the full range of movement of the ankle block member through the three body planes so that the movements of the ankle block member match the anatomical limits of movement of the natural human ankle.

An elongated tibial component has a lower tibial end attached to the universal joint and extends upwardly through that part of the aperture which registers with the ankle block member upper surface so that an upper tibial end can be attached to a tibial shock member. The length of the tibial component can be varied for each individual amputee.

The tibial shock member of the present invention is either an adjustable or self-compensating device which allows for shock absorption during the contact period of the gait cycle. The tibial shock member absorbs the shock that's normally transmitted during the contact period and limits the amount of shock transmitted to the hip, pelvis, lumbar spine, cerebrospinal fluid and brain with conventional prosthetic devices. The tibial shock member also facilitates the smoothness of the amputee's gait by working in concert with a heel shock member to allow a modest return of stored energy at the heel strike phase of the gait cycle. Furthermore, the tibial shock member has an integrally attached upper threaded end which is mounted to other structural elements hereinafter described.

In addition, the heel shock member is mounted to the rear side of the ankle block member for providing shock absorption during the heel strike contact period of the gait cycle, and the heel shock member is mounted to the rear side of the ankle block member at an angle which matches the angle at which the natural human heel strikes the terrain during the heel strike contact period of the gait cycle. Both the heel shock member and the tibial shock member are adjustable to allow the amputee to engage in a wide range of activities.

In order to properly align and match the pitch and angle of the prosthetic device with the pitch and angle of the amputee's natural leg so that the gait of the amputee corresponds to his or her normal walking rhythm, the prosthetic device includes a gait adjustment means. The stump of the amputee is fitted with a socket or receiver having infixed studs projecting downwardly therefrom. The receiver encompasses the stump and a portion of the amputee's leg. The gait adjustment means is adapted for removable securement to the studs, and the upper threaded portion of the tibial shock member is adapted for removable securement to the gait adjustment means.

The primary structural elements of the gait adjustment means are an upper mounting block attached subjacent and contiguous to the receiver's flat undersurface and a lower mounting block spaced from and subjacent to the upper mounting block. The upper and lower mounting blocks are in vertical axial alignment to each other when disposed in their operative position, and the lower mounting block is attached to the upper mounting block by fasteners that extend downwardly through the upper mounting block and also through the lower mounting block. The lower mounting block further includes a centrally-located threaded bore for receiving the upper threaded portion of the tibial shock member. The upper mounting block further includes a centrally-located unthreaded bore axially aligned with the threaded bore of the lower mounting block when both mounting blocks are disposed in the operative position. The unthreaded bore of the upper block has a greater diameter than both the threaded bore of the lower block and the upper threaded portion of the tibial shock member.

When disposed in their operative positions, the mounting blocks are located in parallel, horizontal planes with a clearance space between them to allow for adjustment of the lower block with respect to the upper block. More specifically, when the components of the prosthetic device are assembled together and the device is attached to the amputee's stump via the receiver, the lower block is adapted for selective adjustability in a plurality of planes non-parallel to the horizontal plane of the upper block, and this adjustability allows the close matching of the pitch and angle of the prosthetic device with the pitch and angle of the amputee's natural leg.

The prosthetic device of the present invention further includes a lateral, elongated metatarsal bar and a medial, elongated metatarsal bar, the lateral metatarsal bar pivotally mounted to the ankle block member lateral side and the medial metatarsal bar pivotally mounted to the ankle block member medial side. The medial and lateral metatarsal bars correspond to the medial and lateral members of the natural human foot, and are joined by a metatarsal connecting bar pivotally mounted to the distal ends of the metatarsal bars. The metatarsal bars establish the medial and lateral limits of the ankle block member, work in conjunction with the metatarsal connecting bar to facilitate the ability of the amputee to stand on uneven ground, and assist in evenly distributing weight about the ankle block member during the gait cycle.

It is an objective of the present invention to provide a prosthetic device comprised of numerous structural components which are easily replaceable to minimize repair costs.

Another objective of the present invention is to provide a prosthetic device wherein the structural components are manufactured from lightweight durable materials such as polycarbonates and other composites, aluminum, titanium, or phenolics.

Yet another objective of the prosthetic device of the present invention is to provide structural components whose movements simulate the movements of a natural human leg, ankle, and foot throughout the various phases of the gait cycle.

Other features, objects, and characteristics of the prosthetic device of the present invention will be understood and appreciated from the ensuing detailed description of the several preferred embodiments of the invention, when read with reference to the accompanying drawings.

BRIEF DESCRIPTION OF THE DRAWINGS

FIG. 1 is an exploded isometric view of the preferred embodiment of the ankle, foot, and lower leg prosthetic device of the present invention;

FIG. 2 is a side elevational view of the prosthetic device first shown in FIG. 1, illustrating its attachment to the stump of an individual;

FIG. 3 is a perspective view of a human body for illustrating the three body planes into which the human body is divided;

FIG. 4 is an enlarged fragmentary view of features first shown in FIG. 3, illustrating the three body planes into which the human ankle and foot are divided;

FIG. 5A is an enlarged perspective view of the physical movement known as inversion;

FIG. 5B is an enlarged perspective view of the physical movement known as eversion;

FIG. 5C is an enlarged perspective view of the physical movement known as plantarflexion;

FIG. 5D is an enlarged perspective view of the physical movement known as dorsiflexion;

FIG. 5E is an enlarged perspective view of the physical movement known as pronation; and FIG. 5F is an enlarged perspective view of the physical movement known as supination.

FIG. 6 is a side elevational view of the human body going through the successive phases of the gait cycle;

FIG. 7 is an enlarged fragmentary perspective view of structural components of the device first shown in FIG. 1;

FIG. 9 is a top plan view of structural components of the device first shown in FIG. 1 as they would appear if attached to the right leg stump of a lower extremity amputee;

FIG. 10 is a top plan view of structural components of the device first shown in FIG. 1 as they would appear if attached to the left leg stump of a lower extremity amputee;

FIG. 11 is a rear elevational view of structural components of the device first shown in FIG. 1;

FIG. 12 is a side elevational view of structural components of the device first shown in FIG. 1;

FIG. 13 is an enlarged front elevational view of the metatarsal head member of the device first shown in FIG. 1, illustrating an alternate embodiment for the helical toe spring;

FIG. 14 is an enlarged side elevational view of the metatarsal head member of the device first shown in FIG. 1, illustrating the attachment thereto by the leaf spring;

FIG. 15 is a bottom plan view of the metatarsal head members first shown in FIG. 1, illustrating the attachment thereto by leaf springs;

FIG. 16 is an enlarged perspective view of the device first shown in FIG. 1, illustrating an alternate embodiment for the universal joint.

DETAILED DESCRIPTION OF THE PREFERRED EMBODIMENT

Figure 8:
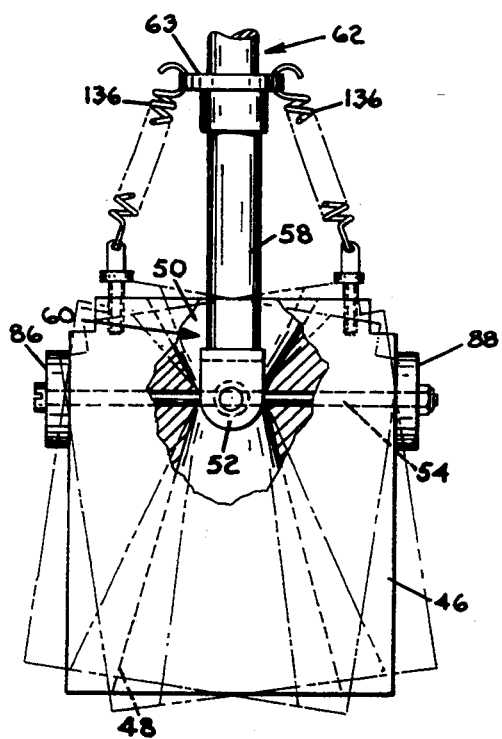
FIG. 8 is a front elevational view of structural components of the device first shown in FIG. 1.

FIGS. 1 and 2 illustrate an ankle, foot, and lower leg prosthetic device 10 for simulating the movements of the natural human ankle and foot throughout all phases of the gait cycle and which is adapted for the removable securement to a stump 12 of a lower extremity amputee. Foot amputations may be divided into several levels. One type of amputation for which the device 10 is adapted is the Syme amputation which results in the removal of an entire foot. A lower extremity amputee has a foot removed as well as a portion of the lower leg, terminating at or immediately below the knee. The portion of the leg remaining is called the "stump". The stump fits into a receiver or stump socket which is made of a lightweight and durable synthetic material. The inventors of the device 10 have also conceived a stump socket 140 shown in FIG. 2, which is custom-fitted to each individual user. The device 10 functions as a system for simulating the anatomical movements of the natural human ankle and foot, and has a number of features making it advantageous over the prior art. For example, the resistance of all shock absorbers incorporated into the device 10 are adjustable for accommodating each individual user. Further, the device 10 is comprised of a number of component parts or systems which are easily replaceable and which, therefore, limits repair costs. In addition, the device 10 is manufactured from a number of lightweight, durable materials, such as polycarbonates, aluminum, titanium, and phenolics. Also, the movements of the various components which comprise the device 10 closely simulate the movements of the actual leg, ankle, and foot when they are disposed in gait on any walking surface. For example, one of the most difficult stances for a lower extremity amputee fitted with a prosthetic device is to stand or ambulate on an uneven walking surface or terrain. The device 10 is designed to overcome this shortcoming of prior art prosthetic devices. Furthermore, the secure and comfortable fit for each user is achieved by sizing and fitting the device 10 and the stump socket 14 to each individual user. Finally, the structural component which simulates the natural human ankle allows smooth forward, lateral, and rearward movement throughout the three body planes to the anatomical limits of the natural human ankle.

In order to more fully understand and appreciate the advantages of the device 10 over the prior art, it is necessary to provide some basic biomechanical terminology. As indicated in FIGS. 3 and 4, there are three reference planes in the human body 16; and each reference plane is perpendicular to the other two planes. The sagittal plane 18 is a vertical plane passing through the human body 16 from front to back and which divides the human body 16 into a right half and a left half. The frontal plane 20 is a vertical plane that passes through the human body 16 from side to side and which divides the human body 16 into a front half and a back half. Finally, the transverse plane 22 is a horizontal plane which passes through the human body 16 from side to side and from front to back, dividing the human body 16 into an upper half and a lower half. Bodily motion can occur in all three of these reference planes 18, 20, and 22, and all motion has an axis; an axis being simply an invisible line around which motion takes place. Body motion takes place in one plane and the axis lies in the other two planes. The frontal-transverse axis 24 is horizontal in nature and passes from side to side and lies in the frontal and transverse planes. The motion that occurs around this axis is always a sagittal plane motion. The sagittal-transverse axis 26 is a horizontal axis that passes from front to back and lies in the sagittal and transverse planes. The body motion that occurs around this axis is always frontal plane motion. The frontal-sagittal axis 28 is a vertical axis that is perpendicular to the ground and lies in the frontal and sagittal planes. The motion that takes place around this axis is always a transverse plane motion.

FIG. 5 illustrates the basic movements of the natural human ankle that are matched by the ankle block component of the device 10. From left to right, the basic movements of the foot are: [1] inversion 30—the movement of the ankle that allows one to walk on the outside (lateral) edge of the foot as the bottom of the foot goes in and the stress is on the outside (lateral side) of the foot; [2] eversion 32—the movement that allows an individual to walk on the inside (medial) edge of the foot as the bottom of the foot goes out and the stress is on the inside (medial side) of the foot; [3] plantarflexion 34—the movement of the foot observed when one extends the ankle and the toes downward (this is the movement necessary for toe walking and is also the movement seen when an individual walks downhill); [4] dorsiflexion 36—the movement of the foot observed when one draws the top of the foot toward the front of the leg as the individual extends the toes upward for walking uphill; [5] pronation 38—that movement of the foot observed when one plantarflexes the ankle and externally rotates the leg; and [6] supination 40—that movement observed when one plantarflexes the ankle and internally rotates the leg.

The device 10 is designed to simulate the movements of an actual human ankle and foot throughout all the phases of the gait cycle. Reference will be made to FIG. 6 to explain the various phases of the gait cycle 42. Human beings have evolved bipedalism as the most efficient means of locomotion over any walking surface 44. Bipedal gait is the repetitive sequence of alternating movements of the lower limbs, and one complete sequence for both lower limbs represents a gait cycle. The main subdivisions of the gait cycle 42 are the stance phase and the swing phase. The stance phase represents that period of ground contact and weight support of the foot, and the swing phase represents that portion of the gait cycle when the same foot is off the ground. The stance phase comprises roughly 62% of the gait cycle and the swing phase comprises roughly 38% of the gait cycle. The stance phase of the gait cycle is further subdivided into the contact period, the mid-stance period, and the propulsive period. The contact period is initiated by the heel strike wherein the foot is lowered to the ground as the body moves from a posterior position to one directly over the foot. The fully loaded foot—or foot flat—begins the mid-stance period when it singly bears the body weight and the alternate foot is in the swing phase. A continuation of the forward shifting body results in the lifting of the heel—heel off—and the initiation of the propulsive period. During the propulsive period, the body weight is shifted to the toes and, at the end, the alternate foot regains contact with the ground by heel strike. The propulsive period ends with toe off when the foot is lifted from the ground, initiating swing phase. During swing phase, the limb is brought forward for heel striking again, completing a gait cycle. FIG. 6 illustrates an individual's locomotion through the gait cycle 42, and, from right to left, the gait positions of the individual are heel strike, forefoot loaded, heel lift, and toe off. The heel strike, forefoot loaded, and heel lift positions occur in the stance phase of the gait cycle, and the toe off position initiates the swing phase of the gait cycle.

As shown in FIGS. 1, 20 and 8-12, there is shown an ankle block component which is the central feature and heart of the device 10. The ankle block component is an ankle block member 46 which simulates the movements of a natural human ankle to the anatomical limits of the natural human ankle. The ankle block member 46 simulates the basic movements of the natural human ankle—inversion 30, eversion 32, dorsiflexion 34, plantarflexion 36, pronation 38, and supination 40—and any combination of these movements due to the design of the ankle block member 46. The ankle block member 46 may be either square-shaped or rectangular-shaped and includes a front side, a rear side, a lateral side, a medial side, an upper surface, and lower surface. The medial side of the ankle block member 46 is that side which is closest to the sagittal plane 18 of the human body 16 as shown in FIGS. 3 and 4, and the lateral side of the ankle block member 46 is that side which is furthest from the sagittal plane 18 of the human body 16 as shown in FIGS. 3 and 4. The ankle block member 46 is adapted to move throughout the three bodily planes as shown in FIGS. 3 and 4, and is manufactured from a lightweight, durable material, such as a polycarbonate, titanium, aluminum, or other various composite materials. When an individual is standing erect at the beginning of the gait cycle 42, the ankle block member 46 will be disposed with its lower surface parallel to the walking surface 44.

As shown in FIGS. 1, 9, 10, and 16, a chamber extends through the ankle block member 46 generally from the central portion of the ankle block member 46 upward for registering with the upper surface so that the chamber is located on a vertical axis perpendicular to the walking surface 44. The chamber can be an hourglass-like aperture 48 which extends through the ankle block member 46 and registers with the upper surface as shown in FIG. 1, or, in an alternate embodiment, as shown in FIG. 16, the chamber can be a generally centrally-located, upwardly-opening, concave-shaped aperture 50 which registers with the upper surface of the ankle member 46. In either case, the diameters of the apertures 48 and 50 at the point where they register with the upper surface defines the anatomical limits of movement of each ankle block member 46. Although not shown in any of the figures, in order to reduce the weight of the ankle block member 46 voids can be drilled through the ankle block member 46 from the medial side to the lateral side and these voids would have the shape of cylindrical passageways extending through the entire ankle block member 46.

Referring to FIGS. 1 and 8, a universal joint 52 is disposed within the aperture 48 at the narrowest portion of the aperture 48. An anchoring pin or rod 54 is inserted through the ankle block member 46 from the medial side to the lateral side, and the rod 54 is aligned so that it passes through the narrowest portion of the aperture 48. The joint 52 is pinned and secured to the rod 54 so that the joint 52 can rotate about the axis of the rod 54. In other words, the joint 52 is pinned to the rod 54 on a horizontal plane, and the joint 52 rides upon the rod 54 within the narrowest portion of the aperture 48. It is the joint 52 which allows the full range of movement of the ankle block member 46 in the three body planes 18, 20, and 22 so that the range of movements of the ankle block member 46 simulates the movements to the anatomical limits of the natural human ankle. The joint 52 allows the ankle block member 46 to move in the three body planes 18, 20, and 22, and gives the amputee the ability to stand or walk on uneven walking surfaces. The width of the aperture 48 where it registers with the upper surface of the ankle block member 46 represents the maximum limit of movement of the ankle block member 46.

Referring to FIG. 16, there is shown the alternate embodiment of the chamber which is channeled and formed out of the ankle block member 46. FIG. 16 illustrates the aperture 50 which registers with the upper surface of the ankle block member 46 and defines the anatomical limits of movement of the ankle block member 46. However, instead of utilizing the joint 52, as shown in FIG. 1, the ankle block member 46 shown in FIG. 14 utilizes a ball joint 56. The ball joint 56 is firmly seated within the aperture 50 at the lowest point thereof for allowing the full range of movement of the ankle block member 46 in the three body planes 18, 20, and 22 so that the movements of the ankle block member 46 simulate the movements of the natural human ankle to the anatomical limits of the natural human ankle.

Referring to FIGS. 1 and 8-12, there is shown a means for attaching the joint 52 to structural elements of the device 10 which will be hereinafter further described. Specifically, the attaching means is an elongated tibial component 58 which has a lower tibial end 60 secured to the joint 52 and an upper tibial end 62 adapted for removable securement to a structural component which will be hereinafter further described. The component 58 is a cylindrical shaft which extends up through the aperture 48 and is perpendicular to the surface 44 when the amputee is standing upright on the surface 44 and the ankle block member 46 is disposed parallel therewith. The length of the component 58 can be sized to fit each individual lower extremity amputee, and, as shown in FIGS. 2, 11, and 12, a keyed slot 64 is located at the end 62 thereof. It should be noted that the component 58 does not rotate but is rigidly secured at its end 60 to the joint 52.

Shown in FIGS. 1, 2, 9-12, and 17 is an upper mounting collar 63 which is placed on the component 58 at the end 62. The collar 63 is slipped onto the end 62 and can either be fixedly mounted by a set screw or may be spring-mounted by having an internally mounted coil spring which encompasses and mounts to the component 58. The collar 63 includes an annular flange of greater diameter than the collar 63, and the flange has apertures formed through its peripheral edge at equally-spaced increments of 90°, the purpose of which will be hereinafter further described.

Figure 17:
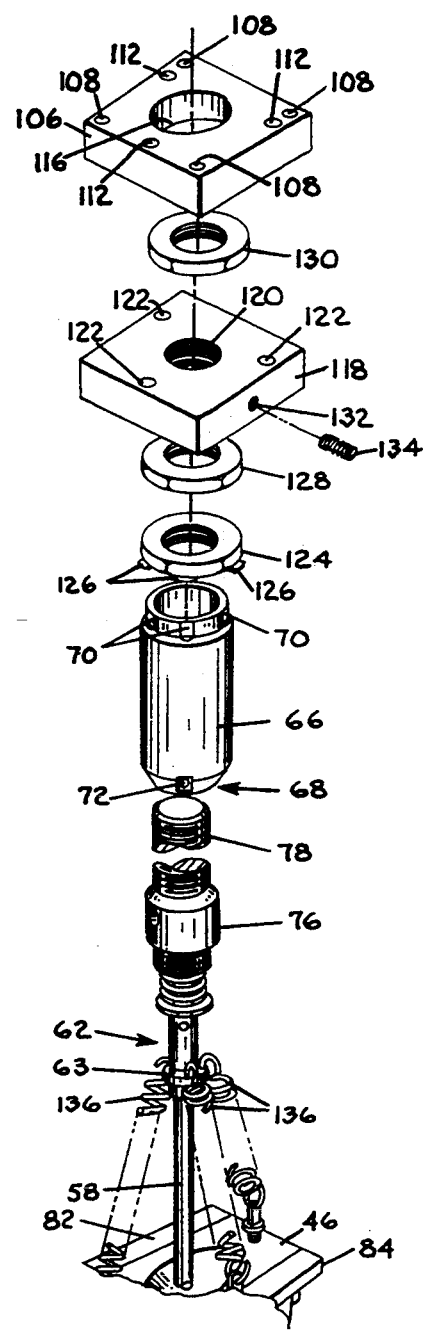
FIG. 17 is an exploded isometric view of the device first shown in FIG. 1, illustrating the tibial shock member.

Referring to FIGS. 1, 2, and 17 there is shown an anti-rotation collar 66 which is adapted for removable securement to the end 62. The collar 66 is a cylindrical object which is tapered at its bottom end 68 and has a cylindrical chamber extending through the length of the collar 66. The collar 66 includes a series of equally spaced-apart flats 70 adjacent an upper rim and a threaded through-hole 72 perpendicular to the cylindrical chamber located at the opposite tapered end 68.

The through-hole 72 at the tapered end 68 of the collar 66 is adapted to receive a set screw 74 which is inserted through the through-hole 72 into the slot 64 at the end 62. When the set screw 74 is inserted into the slot 64, the component 58 is prevented from rotating and is firmly attached to the collar 66. As will be more fully explained hereinafter, the slot 64 in the preferred embodiment allows limited travel upward and downward along the vertical axis of the component 58; the length of the slot 64 can be varied to suit individual users but the slot 64 is necessary to allow the reciprocal upward and downward movement of the component 58.

Referring to FIGS. 1, 2, and 17, there is shown a tibial shock member 76 having an upper threaded portion 78 integrally formed therefrom and extending upward and opposite the component 58 when the member 76 is disposed in its operative position. The member 76 is a spring-assisted hydraulic shock which may be either manually adjustable or self-compensating to permit the amputee to pursue vigorous physical activity without sustained potential physical damage. The member 76 allows for shock absorption during the contact period of the gait cycle 42, and limits the amount of shock that is normally transmitted during the contact period to the stump, hip, pelvis, lumbar spine, and cerebrospinal fluid. Moreover, the compressibility of the member 76 limits the necessity for Trendelenburg gait which is a method of walking with a prosthesis that necessitates swinging the prosthesis laterally and forward in gait. The member 76 is snugly and securely installed within the collar 66 so that only an upper threaded end 78 will project outwardly therefrom, as shown in FIG. 1. However, the end 78 is adapted for removable subjacent attachment to structural elements hereinafter further described. Also, the length of the end 78 can be sized to fit the height of each individual user, and when the device 10 is fully assembled the center of the joint 52, the component 58, the collar 66, the shock member 76, and the end 78 are all in vertical axial alignment perpendicular to the surface 44 when the amputee is standing erect thereon.

Referring to FIGS. 1, 9-12, and 16, another structural component which assists in shock absorption is a heel shock member 80. The member 80 provides shock absorption at heel strike which is part of the contact period of the stance phase of the gait cycle 42. The member 80 is mounted at an angle matching the angle at which the normal human heel strikes the surface 44 at heel strike in the gait cycle 42. The member 80 is mounted to the rear side of the ankle block member 46 and can be either flange-mounted or screw-mounted directly into the rear side of the ankle block member 46. In addition, the member 80 causes the ankle block member 46 to roll to the plantarflexed position 34 in order to transfer the weight of the individual during the stance phase of the gait cycle 42. Like the tibial shock member 76, the heel shock member 80 is an adjustable component to allow for different activities by each individual user.

Referring to FIGS. 1, 9-12, 16, and 17, there are shown a number of structural components which simulate the workings and movements of the natural human foot. More specifically, simulating the first and the fifth metatarsals are, respectively, a first medial metatarsal component 82 and a fifth lateral metatarsal component 84, both of which are secured to the ankle block member 46 adjacent the portion of the aperture 48 which registers with the upper surface. The components 82 and 84 may be secured to the ankle block member 46 by having threaded fasteners inserted through each respective component 82 and 84 and into the body of the ankle block member 46 itself. The components 82 and 84 will be manufactured from the same material (polycarbonate or composite material, for example) as the ankle block member 46. The medial and lateral metatarsal components 82 and 84 establish the medial and lateral limits of the prosthetic device 10 and match the medial and lateral limits of the natural human foot. As shown in FIG. 1, the components 82 and 84 project slightly forward of the front side of the ankle block member 46.

Again, referring to FIGS. 1, 9-12, and 16, there is shown a pair of spaced-apart, elongated metatarsal bars which project past the respective components 82 and 84 and are pivotally mounted to the ankle block member 46. More specifically, the device 10 includes a medial metatarsal bar 86 mounted to the medial side of the ankle block member 46 beneath the component 82 and a lateral metatarsal bar 88 pivotally mounted to the lateral side of the ankle block member 46 immediately adjacent and beneath the component 84. The pivotal movement of each bar 86 and 88 is in a plane perpendicular to the flat surface 44 throughout the stance phase and swing phase of the gait cycle 42. Although it is not shown in any of the figures, the bars 86 and 88 may have a number of spaced-apart holes drilled through their respective widths in order to reduce their weight.

In order to control and delimit the pivotal movement of the bars 86 and 88, and to insure proper functioning of the device 10 when it is used by a lower extremity amputee, a pair of metatarsal shock members 90 and 92 must be attached to the components 82 and 84 and bars 86 and 88. More specifically, as shown in FIGS. 1, 12, and 16, the member 90 extends between and is attached to the distal end of the component 82 and the bar 86. The member 90 is pivotally mounted to the distal end of the component 82 and has an opposite end pivotally mounted to the bar 86 at approximately its mid-point. The member 92 is pivotally mounted to the distal end of the component 84 and has an opposite end pivotally mounted to the bar 88 at approximately the mid-point thereof. The metatarsal shock members 90 and 92 are similar to the tibial shock member 76 and the heel shock member 80 in that their dampening ability can be adjusted to accommodate each individual user of the prosthetic device.

Another structural feature which is necessary for the prosthetic device to simulate a natural human foot is metatarsal head components. As shown in FIGS. 1, 9, 10, and 12-15, the device 10 includes a pair of metatarsal head members. A medial metatarsal head member 94 is pivotally secured to the distal end of the bar 86 and a lateral metatarsal head member 96 is pivotally secured to the bar 88 at its distal end. Both members 94 and 96 are mounted to the respective bars 86 and 88 by mounting pins extending through the bars 86 and 88 and inserted into each member 94 and 96. The members 94 and 96 pivot or rotate on their mounting pins to match the anatomical limits of the human phalanges. The members 94 and 96 are cylindrical structures which strike the surface 44 when the individual is in the toe off propulsive period of the stance phase of the gait cycle 42.

In order to facilitate locomotion by the individual during the gait cycle 42, a structural feature is mounted to each respective member 94 and 96 in order to permit transfer of energy into the normal walking gait before the toe off position of the gait cycle 42 and also to allow the device 10 to roll over before the toe off propulsive period of the stance phase and into the swing phase of the gait cycle 42. The structural features which facilitate achieving these results are toe spring components which are mounted to each respective member 94 and 96. Referring to FIGS. 1, 9, and 10, there is shown a preferred embodiment of the induction means for storing, transferring, and releasing energy during the various phases of the gait cycle 42 in order to simulate the transfer of energy that occurs in the natural human foot during the swing and the stance phases of the gait cycle 42. The induction means illustrated in FIGS. 1, 9, 10, and 12 are a pair of helical toe springs 98 attached to each respective member 94 and 96 and projecting forwardly therefrom and parallel to the surface 44. The springs 98 are capable of storing and releasing energy during the toe off stance phase of the gait cycle 42 and transferring energy as the amputee's body weight shifts from the stance phase to the swing phase of the gait cycle 42.

An alternate preferred embodiment of the induction means is illustrated in FIGS. 13-15. The alternate preferred embodiment of the induction means is a pair of leaf springs 100 with one spring 100 adapted for slidable and adjustable attachment at the bottom of the member 96 and the other spring 100 adapted for slidable and adjustable attachment to the bottom of the member 94. Both springs 100 perform the same function as the springs 98: they store and release energy during the toe off stance phase of the gait cycle 42 and transfer energy as the amputee's body weight passes over a center line perpendicular to the surface 44 during the mid-stance period of the stance phase of the gait cycle 42.

In addition and to further assist and control locomotion for the amputee, working in conjunction with the bars 86 and 88 is a metatarsal connection bar 102. As shown in FIGS. 1, 9, 10, and 15, the bar 102 extends between and has opposed ends pivotally mounted to each respective member 94 and 96. The bar 102 is mounted to each member 94 and 96 by, for example, a swivel, and the pivotal movement of the bar 102 operates in conjunction with the pivotal movement of the bars 86 and 88 to perform two essential functions: (1) allowing for independent pivotal movement of the bars 86 and 88; and (2) facilitating an even distribution of weight about the bars 86 and 88, and the ankle block member 46, during the various phases of the gait cycle 42 that closely matches the distribution of weight in the natural human foot.

In order to attach the device 10 to the stump 12 it is necessary to fit the stump socket 14 to the stump 12, which can be done in a number of ways well known in the art. It is extremely important that the socket 14 be cast while the stump 12 is in a weight-bearing disposition of insertion within the cast for the socket 14 to insure a highly accurate fit for each individual amputee since each socket 14 will be individually cast and custom fitted for each individual lower extremity amputee.

The socket 14 is adapted for insertion on, and removable attachment to, the amputee's stump 12. The socket 14 will completely encompass the stump 12 and will actually be attached to a remaining portion of the leg above the stump 12. Because the socket 14 is cast while in a weight-bearing disposition of insertion on the stump 12, a number of advantages follow therefrom: the stump 12 is comfortably fitted within the socket 14; there is less likelihood of skin breakdown, stump sores, and excoriation; rotation of the stump 12 within the socket 14 is limited due to the snug fit; and the custom designed socket 14 unitizes the stump 12 to the device 10. As shown in FIG. 2, the socket 14 has a slight, centrally-located indentation or convex depression formed on its undersurface. The bottom of the socket 14 terminates at the flat undersurface from which four spaced-apart infixed studs 104 downwardly project to the surface 44 when the socket 14 is attached to the stump 12.

Because the normal walking gait of each individual is unique, the device 10 must include a means for making very fine adjustments to properly align and match the pitch and angle of the device 10 with the pitch and angle of the amputee's natural leg so that the normal walking gait of the amputee corresponds to his or her normal walking rhythm. For example, if the amputee is slightly bow-legged and the device 10 is attached to the amputee's stump 12 so that the device 10 extends perpendicular to the surface 44, the normal walking gait of the amputee will be disrupted because of misalignment between the device 10 and the amputee's remaining natural leg. Specifically, the device 10 includes a gait adjustment means which compensates for this misalignment between the amputee's remaining natural leg and the device 10. The gait adjustment means permits the device 10 from the member 76 and all structural components therebelow to be tilted or angled as a unit medially or laterally to compensate for the particular pitch and angle of the amputee's remaining natural leg. If the device 10 was disposed on the surface 44 and an imaginary vertical perpendicular line was projected through the component 58, the member 76, the end 78, and the joint 52, the gait adjustment means would allow the selective angled adjustment radially away from this perpendicular vertical line so that the device 10, when attached to the stump 12, could be matched to the pitch of the amputee's natural leg, thus resulting in the device 10 being aligned in gait with the natural leg. For example, to compensate for knock-knee, the gait adjustment means would be finely adjusted so that the device 10 would be angled out, or laterally, a certain number of degrees away from the amputee's natural knee. The only time it would not be necessary to utilize the gait adjustment means would be in the case of an individual having two perfectly straight legs with respect to the surface 44—and this would be a medical rarity. The gait adjustment means does not permit an infinite amount of angled radial adjustment of the device 10, but it does allow for a wide range of angled, radial adjustment; and, furthermore, the gait adjustment means of the present invention helps to eliminate the peg leg-type of design of previous prosthetic devices.

Referring to FIGS. 1, 2, and 7, the gait adjustment means of the present invention includes an upper mounting block 106 which is adapted for removable securement contiguous to the undersurface of the socket 14. The block 106 includes four non-threaded through-holes 108, each of which is aligned with a respective infixed stud 104 so that the block 106 can be inserted thereon. After the block 106 is inserted onto the studs 104 protruding from the undersurface of the socket 14, locking or mounting nuts 110 are fastened to the tips of each respective stud 104 to firmly secure the block 106 to the socket 14. In addition, the block 106 includes three vertically-extending, threaded through-holes 112 located at 120° increments from each other, and each of these threaded through-holes 112 includes captive or recessed heads which register with the flat upper surface of the block 106. These threaded through-holes 112 are adapted to receive threaded fasteners 114 which have a length greater than the thickness of the block 106 so that the fasteners 114, when disposed in their operative position, can project downward therefrom and completely through the block 106 when fully inserted into each respective through-hole 112. In fact, the length of these fasteners 114 will need to be more than twice the thickness of the block 106. Moreover, the block 106 also includes a centrally-located unthreaded bore 116, as shown in FIGS. 1 and 7, which has a diameter greater than the end 78. When the block 106 is attached to the studs 104, the convex indentation of the socket 14 is axially aligned with the bore 116.

Still referring to FIGS. 1, 2, and 7, the gait adjustment means further includes a lower mounting block 118 which has generally the same dimensions as the block 106. The block 118 includes a centrally-located threaded bore 120 extending therethrough and into which the end 78 is inserted to attach the member 76 to the block 118. The member 76 is adapted for selective linear adjustment with respect to the block 118 by selectively threading, positioning, and repositioning the end 78, as needed, into and, depending upon the height of the individual amputee, completely through the block 118, so a substantial portion of the end 78 projects upwardly therefrom and into the bore 116. In addition, the block 118 includes three non-threaded through-holes 122 extending completely through the block 118 and located at 120° increments from each other.

As shown in FIG. 7, the through-holes 112 and 122 are axially aligned when both blocks 106 and 118 are disposed in their initial operative positions of attachment to the socket 14 in spaced-apart, horizontally-extending parallel planes with respect to each other. Also, the through-holes 122 are oversized and have a greater diameter than the through-holes 112 to permit selective adjustable angular movement of the block 118 with respect to the fixed position of the block 106. The oversized through-holes 122 permit the block 118 to be selectively adjustable in a plurality of planes that are non-parallel to the horizontally-extending plane of the block 106 when the block 106 is firmly secured contiguous to the undersurface of the socket 14 so that the pitch and angle of the device 10 can match the pitch and angle of the amputee's natural leg.

In one method of assembling the gait adjustment means to the undersurface of the socket 14, the fasteners 114 are first threadably inserted completely through the through-holes 112 so that each fastener 114 projects below the block 106 a distance more than twice the thickness of the block 106. Because the through-holes 112 have recessed heads, the heads of the fasteners 114 are flush or may be countersunk with the upper surface of the block 106. With the fasteners 114 threadably inserted into and completely through the block 106, the four through-holes 108 are aligned with the studs 104 and then the block 106 is inserted onto the studs 104 so that each respective stud 104 is received by each respective through-hole 108. Then, nuts 110 and washers are attached to the tip of each respective stud 104 to firmly secure and mount the block 106 contiguous to the undersurface of the socket 14. The three through-holes 122 in the block 118 are then aligned with the fasteners 114 so that these fasteners 114 can be inserted through each respective through-hole 122. A lock nut and lock washer are then attached to the end of each fastener 114 to secure the block 118 to the fasteners 114 so that the block 118 is positioned in spaced parallel relationship to the block 106. There will be a clearance space between the blocks 106 and 118, as shown in FIG. 2, but in this initial position the block 118 will be parallel with the block 106 unlike FIG. 2.

Referring to FIGS. 1 and 2, in order to secure the structural components of the device 10 extending from the springs 98 or 100 to the member 76 to the blocks 106 and 118, several more steps are required. Threaded onto the end 78 is, first, a tab washer 124 with integrally-formed tabs 126 peripherally extending therefrom and then a first locking nut 128. Both the washer 124 and the nut 128 are threaded onto the end 78 and, since this is the initial step in properly mounting them to the end 78, the washer 124 and the nut 128 are, therefore, loosely threaded onto the end 78. The end 78 is then threaded into the bore 120. The end 78 is then inserted completely through the bore 120 so that the end 78 protrudes up through the block 118. A second locking nut 130, as shown in FIG. 1, is then loosely threaded onto the end 78 for initial mounting thereon. In this initial position, the blocks 106 and 118, the nuts 128 and 130, the washer 124, the member 76, the collar 66, and the component 58 are all in axial alignment perpendicular to the surface 44 on which the device 10, now attached to the stump 12 of the lower extremity amputee, is disposed. The fine adjustment of the device 10 to match the pitch and angle of the amputee's natural leg can now occur. Because the height of each individual amputee varies, and the exact point of lower extremity amputation and the subsequent creation and formation of the stump varies from individual to individual, the distance from the block 106 to the underside of the ankle block member 46 will naturally vary from individual to individual. A typical range in distance between the block 106 and the underside of the ankle block member 46 may be between thirteen and one-half inches to eighteen inches. This distance range affects the amount of selective linear adjustment of the end 78 into and through the bore 120 and, if necessary, into and through the bore 116. The oversized bore 116 will permit the end 78 to radially deviate from a vertical axis in the preferred embodiment. Naturally, enlarging the diameter of the bore 116 will permit a greater angled and radial deviation from the vertical axis by the end 78 if the end 78 must be inserted therein to achieve a proper fitting of the device 10 to the particular amputee.

With the device 10 now attached to the stump socket 14, as shown in FIG. 2, the device 10 can be properly adjusted and aligned to match the pitch and angle of the amputee's natural leg. Because the three through-holes 122 are oversized with respect to the portions of the fasteners 114 that extend through them, the block 118 can be selectively adjusted and tilted to a plurality of planes that are non-parallel to the horizontally-extending plane of the block 106. It is a relatively simple matter to tighten either one, two, or all three of the lock nuts which are attached to the ends of the fasteners 114 projecting through the through-holes 122, and tightening these lock nuts either singly or in combination takes up the block 118 and causing it to be tilted in a variety of planes non-parallel to the horizontal plane of the block 106. In other words, the block 118 can be rocked completely forward by tightening the nut secured to the fastener 114 projecting through the oversized through-hole 122 located at the front of the block 118 or the block 118 can be rocked backwards by tightening the lock nuts attached to the fasteners 114 which project through the through-holes 122 at the rear of the block 118. The block 118 can be rocked medially or laterally by tightening different combinations of the lock nuts attached to their respective fasteners 114 extending through the through-holes 122. The degree of angulation of the block 118 from a vertical axis extending perpendicular to the surface 44 and up through the bore 120 would depend on the thickness of the block 118, the diameter of the three through-holes 122, and the amount by which the lock nuts are taken up on the fasteners 114.

The angle to which the block 118 is adjusted is dependent on the individual being sized and the through-holes 122 may be bored for larger diameters to allow for a variety of degrees of angulation of the block 118 from the vertical axis. Increasing the diameter of the through-holes 122 will naturally increase the degrees of angulation of the block 118. Once the proper angulation of the block 118 is attained so that the pitch and angle of the device 10 matches the pitch and angle of the amputee's natural leg for achieving normal walking gait, the nuts 128 and 130 are tightened down upon the block 118 to secure its position of angulation. The washer 124 is then threaded downward on the end 78 to a point where the main body of the member 76 begins so that the tabs 126 themselves can be bent down to contact the flats 70. The block 118 in FIG. 2 is shown for illustrative purposes angled or rocked slightly forward diminishing the clearance space between the front of the blocks 106 and 118; however, there will always be a clearance space between the blocks 106 and 118 as this clearance space also facilitates the tilting and angling of the block 118 with respect to the block 106. The amount of clearance between the blocks 106 and 118 would vary relative to the amount of angulation required for each individual amputee to track appropriately throughout the gait cycle 42. It is only in the extremely rare occurrence of a perfectly straight leg that the blocks 106 and 118 will be disposed in spaced, parallel, horizontally-extending planes with respect to each other after the adjustments have been completed.

With reference to FIGS. 1 and 2, with the tabs 126 bent down and engaging the respective flats 70, and the set screw 74 inserted through the tapered portion 68 of the collar 66 and into the slot 64, the component 58 is locked into place and will not rotate. In addition, FIG. 1 illustrates a set screw 132 inserted into a threaded bore (not shown) in the block 118. The set screw 132 will be inserted through this bore and upon the end 78 that extends through the bore 120. Although it is not shown in FIG. 1, there may be another threaded bore for receiving another set screw 134 which is located 180° opposite of the set screw 132 which is shown on FIG. 1. These set screws 132 and 134 would be tightened down upon the end 78 to further lock the member 76 in place and to prevent the rotation of the member 76.

Referring to FIGS. 1, 2, 8-12, 16, and 17, there is shown a return means for returning the ankle block member 46 to the normal position of being at a right angle to the component 58 when the ankle block member 46 is unweighted during any phase of the gait cycle 42. The return means is necessary to bring the ankle block member 46 back to the normal position every time the device 10 is unweighted, which is when the device 10 is in the air during the swing phase of the gait cycle 42 and also during those periods of the stance phase when the device 10 is not in contact with the surface 44. The return means includes at least four elongated compressible and extensible return springs 136 with each spring 136 having an upper spring end attached to each respective aperture of the annular flange of the collar 63 and a lower spring end attached to the upper surface of the ankle block member 46 immediately adjacent and beside the portion of the aperture 48 which registers with the upper surface of the ankle block member 46. The tension of the springs 136 can be varied by adjusting the fasteners which connect the springs 136 to the ankle block member 46 and by selectively adjusting the placement of the collar 63 on the end 62. Moreover, to insure that the ankle block member 46 is returned to its normal position every time it is unweighted requires that the springs 136 be located at equally spaced increments about the aperture 48, and in the preferred embodiment of the device 10 the springs 136 are located at 90° increments from each other.

As shown in FIG. 2, for obvious cosmetic and safety reasons, the entire prosthetic device 10 will be encased in a covering 138 which simulates the shape and form of a natural human foot and lower leg. The covering 138 may be manufactured from a wide variety of durable synthetic materials that closely simulates human skin. Some common synthetic materials are polyethylene, urethane, or polyurethane. The synthetic external covering material must be flexible, resistant to wear, and easily cleaned. Also, the color of the external covering material should be customized to match the skin tone of the respective user.

The invention may be embodied in other specific forms without departing from the spirit or essential characteristics thereof. The present embodiment is, therefore, to be considered in all respects as illustrative and not restrictive, the scope of the invention being indicated by the appended claims, and all changes which come within the meaning and range of equivalency of the claims are, therefore, intended to be embraced therein.

We claim:

1. A prosthetic device, for simulating the movements of a human ankle and foot throughout the complete gait cycle and which is adapted to be attached to the stump of a lower extremity amputee for allowing bipedal locomotion on any walking surface so that the pitch of the prosthetic device matches the pitch of the amputee's natural leg, comprising:

a stump receiver adapted for insertion on, and removable attachment to, the amputee's stump, the receiver having a flat undersurface from which infixed studs project;

gait adjustment means secured subjacent to the undersurface of the receiver for selective angled adjustment of the prosthetic device away from a line perpendicular to the walking surface so that the pitch of the prosthetic device when attached to the stump matches the pitch of the amputee's natural leg resulting in the prosthetic device being aligned in gait with the natural leg; and the gait adjustment means including:

an upper mounting block adapted for removable attachment to the receiver so that the upper mounting block is contiguous with the undersurface of the receiver when the upper mounting block is disposed in its operative position;

the upper mounting block further comprising a plurality of vertically-extending, threaded through-holes located at 120° increments from each other;

a lower mounting block having a centrally-located threaded bore extending therethrough and which is secured to the upper mounting block;

a plurality of non-threaded through-holes extending through the lower mounting block located at 120° increments from each other, and which are axially aligned with the threaded through-holes of the upper mounting block when both mounting blocks are disposed in their initial operative positions of attachment to the receiver in spaced-apart, horizontally-extending parallel planes with respect to each other.

2. The prosthetic device of claim 1 further comprising a tibial shock member adapted for removable subjacent attachment to the gait adjustment means for absorbing the shock of the prosthetic device striking the walking surface during the contact period of the gait cycle in order to prevent the transfer of shock to other bodily areas of the amputee.

3. The prosthetic device of claim 2 further comprising an elongated tibial component adapted for removable securement subjacent to the tibial shock member, the tibial component having an upper tibial end for securement to the tibial shock member and an opposite lower tibial end.

4. The prosthetic device of claim 3 further comprising an ankle block member attached to the tibial component and having a front side, a rear side, a medial side, a lateral side, and an aperture extending through the ankle block member which registers with an upper surface of the ankle block member and defines the limits of movement of the ankle block member.

5. The prosthetic device of claim 4 further comprising a universal joint disposed within the aperture and mounted to the ankle block member for allowing the full range of anatomical movement of the ankle block member so that the range of movement of the ankle block member simulates the movement to the anatomical limits of the natural human ankle.

6. The prothetic device of claim 5 further comprising a return means for returning the ankle block member to the normal position of being at a right angle to the tibial component when the ankle block member is unweighted during any phase of the gait cycle.

7. The prosthetic device of claim 4 further comprising a heel shock member for providing shock absorption for the prosthetic device, the heel shock member mounted to the rear side of the ankle block member at an angle matching the angle at which the heel of a natural foot would strike the walking surface when initiating the contact period of the gait cycle.

8. The prothetic device of claim 4 further comprising a medial metatarsal component and a lateral metatarsal component both of which are secured to the ankle block member adjacent the aperture and opposite each other, both metatarsal components projecting past the front side of the ankle block member for defining the medial and lateral limits of the prosthetic device.

9. The prosthetic device of claim 4 further comprising a first and a second spaced-apart, elongated metatarsal bar projecting past the metatarsal components with the first metatarsal bar pivotally mounted to the medial side of the ankle block member beneath the medial metatarsal component and the second metatarsal bar pivotally mounted to the lateral side of the ankle block member beneath the lateral metatarsal component, the pivotal movement of each metatarsal bar occurring in a plane which is generally perpendicular to the walking surface.

10. The prosthetic device of claim 9 further comprising a first and a second metatarsal shock member with the second metatarsal shock member extending between and pivotally mounted to the lateral metatarsal component and the second metatarsal bar mounted on the lateral side of the ankle block member and the first metatarsal shock member extending between and pivotally mounted to the medial metatarsal component and the first metatarsal bar located on the medial side of the ankle block member.

11. The prosthetic device of claim 10 further comprising a first and a second metatarsal head member with the first metatarsal head member pivotally secured to the distal end of the medial metatarsal bar and the second metatarsal head member pivotally secured to the distal end of the lateral metatarsal bar.

12. A prosthetic device, for simulating the movements of a human ankle and foot throughout the complete gait cycle and which is adapted to be attached to the stump of a lower extremity amputee for allowing bipedal locomotion on any walking surface so that the pitch of the prosthetic device matches the pitch of the amputee's natural leg, comprising:

a stump receiver adapted for insertion on, and removable attachment to, the amputee's stump, the receiver having a flat undersurface from which infixed studs project;

gait adjustment means secured subjacent to the undersurface of the receiver for selective angled adjustment of the prosthetic device away from a line perpendicular to the walking surface so that the pitch of the prosthetic device when attached to the stump matches the pitch of the amputee's natural leg resulting in the prosthetic device being aligned in gait with the natural leg; and the gait adjustment means including:
an upper mounting block adapted for removable attachment to the infixed studs of the receiver so that the upper mounting block is contiguous with the undersurface of the receiver when the upper mounting block is disposed in its operative position;
the upper mounting block further comprising a plurality of vertically-extending, threaded through-holes located at 120° increments from each other;
a lower mounting block having a centrally-located threaded bore extending therethrough and which is secured to the upper mounting block;
a plurality of non-threaded through-holes extending through the lower mounting block located at 120° increments from each other, and which are axially aligned with the threaded through-holes of the upper mounting block when both mounting blocks are disposed in their initial operative positions of attachment to the receiver in spaced-apart, horizontally-extending parallel planes with respect to each other;
the non-threaded through-holes of the lower mounting block have a greater diameter than the threaded through-holes of the upper mounting block.

13. A prosthetic device, for simulating the movements of a human ankle and foot throughout the complete gait cycle and which is adapted to be attached to the stump of a lower extremity amputee for allowing bipedal locomotion on any walking surface so that the pitch of the prosthetic device matches the pitch of the amputee's leg, comprising:

a stump receiver adapted for insertion on, and removable attachment to, the amputee's stump, the receiver having a flat undersurface from which infixed studs project;

gait adjustment means secured subjacent to the undersurface of the receiver for selective angled adjustment of the prosthetic device away from a line perpendicular to the walking surface so that the pitch of the prosthetic device when attached to the stump matches the pitch of the amputee's natural leg resulting in the prosthetic device being aligned in gait with the natural leg; and the gait adjustment means including:

an upper mounting block adapted for removable attachment to the infixed studs of the receiver so that the upper mounting block is contiguous with the undersurface of the receiver when the upper mounting block is disposed in its operative position;

the upper mounting block further including a plurality of vertically-extending threaded through-holes located at 120° increments from each other and a centrally-located unthreaded bore;

a lower mounting block having a centrally-located threaded bore extending therethrough and which is secured to the upper mounting block;

a plurality of non-threaded through-holes extending through the lower mounting block located at 120° increments from each other, and which are axially aligned with the threaded through-holes of the upper mounting block when both mounting blocks are disposed in their initial operative positions of attachment to the receiver in spaced-apart, horizontally-extending parallel planes with respect to each other;

the non-threaded through-holes of the lower mounting block have a greater diameter than the threaded through-holes of the upper mounting block;

the lower mounting block being selectively adjustable able in a plurality of planes that are non-parallel to the horizontally-extending plane of the upper mounting block so that the pitch and angle of the prosthetic device can match the pitch and angle of the amputee's natural leg.

14. The prosthetic device of claim 13 further comprising a tibial shock member adapted for removable subjacent attachment to the gait adjustment means for absorbing the shock of the prosthetic device striking the walking surface during the contact period of the gait cycle in order to prevent the transfer of shock to other bodily areas of the amputee.

15. The prosthetic device of claim 14 further comprising an elongated tibial component adapted for removable securement subjacent to the tibial shock member, the tibial component having an upper tibial end for securement to the tibial shock member and an opposite lower tibial end.

16. The prosthetic device of claim 15 further comprising an ankle block member attached to the tibial component and having a front side, a rear side, a medial side, a lateral side, and an aperture extending through the ankle block member which registers with an upper surface of the ankle block member and defines the limits of movement of the ankle block member.

17. The prosthetic device of claim 16 further comprising a universal joint disposed within the aperture and mounted to the ankle block member for allowing the full range of anatomical movement of the ankle block member so that the range of movement of the ankle block member simulates the movement to anatomical limits of the natural human ankle.

18. The prothetic device of claim 17 further comprising a return means for returning the ankle block member to the normal position of being at a right angle to the tibial component when the ankle block member is unweighted during any phase of the gait cycle.

19. The prosthetic device of claim 16 further comprising a heel shock member for providing shock absorption for the prosthetic device, the heel shock member mounted to the rear side of the ankle block member at an angle matching the angle at which the heel of a natural foot would strike the walking surface when initiating the contact period of the gait cycle.

20. The prosthetic device of claim 16 further comprising a medial metatarsal component and a lateral metatarsal component both of which are secured to the ankle block member adjacent the aperture and opposite each other, both metatarsal components projecting past the front side of the ankle block member for defining the medial and lateral limits of the prosthetic device.

21. The prosthetic device of claim 20 further comprising a first and a second spaced-apart, elongated metatarsal bar projecting past the metatarsal components with the first metatarsal bar pivotally mounted to the medial side of the ankle block member beneath the medial metatarsal component and the second metatarsal bar pivotally mounted to the lateral side of the ankle block member beneath the lateral metatarsal component, the pivotal movement of each metatarsal bar occurring in a plane which is generally perpendicular to the walking surface.

22. The prosthetic device of claim 21 further comprising a first and a second metatarsal shock member with the second metatarsal shock member extending between and pivotally mounted to the lateral metatarsal component and the second metatarsal bar mounted on the lateral side of the ankle block member and the first metatarsal shock member extending between and pivotally mounted to the medial metatarsal component and the first metatarsal bar located on the medial side of the ankle block member.

23. The prosthetic device of claim 22 further comprising a first and a second metatarsal head member with the first metatarsal head member pivotally secured to the distal end of the medial metatarsal bar and the second metatarsal head member pivotally secured to the distal end of the lateral metatarsal bar.

24. The prosthetic device of claim 23 further comprising an induction means for storing, transferring, and releasing energy during the phases of the gait cycle in order to simulate the transfer of energy that occurs in the natural human foot during the phases of the gait cycle.

25. The prosthetic device of claim 24 wherein the induction means includes a first and a second helical toe spring with the first helical toe spring attached to the first metatarsal head member and the second helical toe spring attached to the second metatarsal head member, both toe springs capable of storing and releasing energy during the toe off phase of the gait cycle and transferring energy as the amputee's body weight shifts during the gait cycle.

26. The prosthetic device of claim 25 wherein the metatarsal head members work in concert with the helical toe springs and the pivotal movement of the metatarsal head members matches the anatomical limits of the phalanges of the human foot.

27. The prosthetic device of claim 24 wherein the induction means includes a first and a second leaf spring with the first leaf spring attached to the first metatarsal head member and the second leaf spring attached to the second metatarsal head member, both leaf springs capable of storing and releasing energy during the toe of phase of the gait cycle and transferring energy as the amputee's body weight shifts during the gait cycle.

28. The prosthetic device of claim 23 further comprising a metatarsal connecting bar extending between and pivotally attached to the first and the second metatarsal head members for facilitating an even distribution of weight about the ankle block member as the ankle block member contacts the walking surface during the phases of the gait cycle.

29. The prosthetic device of claim 18 wherein the return means includes a plurality of elongated compressible and extensible return springs with each return spring having an upper spring end attached to the upper tibial end of the elongated tibial component and a lower spring end attached to the upper surface of the ankle block member adjacent the aperture.

* * * * *